United States Patent [19]

Cölln et al.

[11] 4,424,168
[45] Jan. 3, 1984

[54] PREPARATION OF α-CYANO-3-PHENOXY-BENZYL 3-ALKENYL-2,2-DIMETHYL-CYCLO-PROPANECARBOXYLATES

[75] Inventors: Reimer Cölln; Bernd Gallenkamp; Hans-Joachim Diehr, all of Wuppertal, Fed. Rep. of Germany

[73] Assignee: Bayer Aktiengesellschaft, Leverkusen, Fed. Rep. of Germany

[21] Appl. No.: 417,766

[22] Filed: Sep. 13, 1982

[30] Foreign Application Priority Data

Oct. 2, 1981 [DE] Fed. Rep. of Germany ....... 3139314

[51] Int. Cl.³ .......................................... C07C 121/75
[52] U.S. Cl. ................................................. 260/465 D
[58] Field of Search .................................... 260/465 D

[56] References Cited

U.S. PATENT DOCUMENTS

| 3,835,176 | 9/1974 | Matsav et al. | 260/465 D |
| 4,110,360 | 8/1978 | Sheldon et al. | 260/465 D |
| 4,123,451 | 10/1978 | Sheldon et al. | 260/465 D |
| 4,280,965 | 7/1981 | Hartmann | 260/465 D |
| 4,350,640 | 9/1982 | Fuchs et al. | 260/465 D |

FOREIGN PATENT DOCUMENTS

| 9792 | 4/1980 | European Pat. Off. |
| 25025 | 1/1981 | European Pat. Off. |
| 33160 | 8/1981 | European Pat. Off. |
| 2709264 | 9/1978 | Fed. Rep. of Germany |

*Primary Examiner*—Dolph H. Torrence
*Attorney, Agent, or Firm*—Sprung, Horn, Kramer & Woods

[57] ABSTRACT

A process for the preparation of a known pesticidal α-cyano-3-phenoxy-benzyl 3-alkenyl-2,2-dimethyl-cyclopropanecarboxylate of the general formula

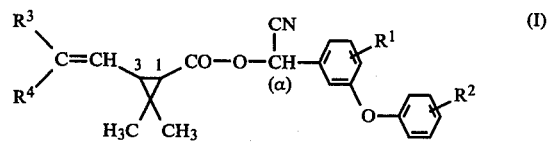

in which $R^1$ and $R^2$ independently of each other represent a hydrogen or halogen atom, $R^3$ represents a hydrogen or halogen atom or an optionally substituted alkyl group, and $R^4$ represents a halogen atom, an optionally substituted alkyl or alkenyl radical or an optionally substituted phenyl group, or, together with $R^3$, represents an alkanediyl (alkylene) radical, comprises reacting a 3-alkenyl-2,2-dimethyl-cyclopropanecarboxylic acid-chloride of the general formula

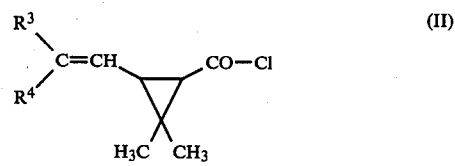

with a 3-phenoxy-benzaldehyde of the general formula

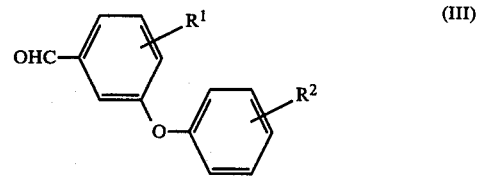

—or an adduct thereof with an alkali metal bisulphite (hydrogen sulphite or pyrosulphite)—and an alkali metal cyanide, using an alkyl ester of a $C_1$ to $C_6$ carboxylic acid and water as diluents, if appropriate with the addition of an alkali metal bisulphite, at a temperature between $-5$ and $+25°$ C. The compounds of formula (I) may be so produced with a high proportion of the more pesticidally active isomers present.

12 Claims, No Drawings

PREPARATION OF α-CYANO-3-PHENOXY-BENZYL 3-ALKENYL-2,2-DIMETHYL-CYCLO-PROPANECARBOXYLATES

The invention relates to an unobvious process for the preparation of certain known pesticidal α-cyano-3-phenoxybenzyl 3-alkenyl-2,2-dimethyl-cyclopropanecarboxylates.

It is known that α-cyano-3-phenoxy-4-fluorobenzyl (cyclo-)-alkanecarboxylates, such as α-cyano-3-phenoxy-4-fluoro-benzyl 3-(2,2-dichloro-vinyl)-2,2-dimethyl-cyclopropane-1-carboxylate or 3-(2-chloro-2-(4-chloro-phenyl)vinyl)-2,2-dimethyl-cyclopropanecarboxylate, or α-cyano-3-phenoxy-4-fluoro-benzyl α-isopropyl-α-(4-chloro-phenyl)acetate, are obtained when the corresponding acid-chlorides, such as 3-(2,2-dichloro-vinyl)-2,2-dimethyl-cyclopropane-1-carboxylic acid-chloride or 3-(2-chloro-2-(4-chlorophenyl))-vinyl-2,2-dimethyl-cyclopropane-1-carboxylic acid-chloride or α-isopropyl-α-(4-chloro-phenyl)-acetic acid-chloride, are reacted with α-cyano-3-phenoxy-4-fluorobenzyl alcohol (see DE-OS'en (German Published Specification) Nos. 2,709,264 and 2,730,515).

However, the yield and quality of the products are unsatisfactory in this preparation process. The cause of this may lie mainly in the fact that the α-cyano-3-phenoxy-4-fluoro-benzyl alcohol employed as the starting compound decomposes very readily into the starting components 3-phenoxy-4-fluoro-benzaldehyde and hydrogen cyanide, and is virtually impossible to prepare in pure form.

Furthermore, it is known that substituted α-cyano-benzyl cyclopropanecarboxylates are obtained when substituted cyclopropanecarboxylic acid-halides are reacted with substituted benzaldehydes in the presence of aqueous solutions of sodium cyanide or potassium cyanide (see DE-OS (German Published Specification) No. 2,231,312/U.S. Pat. No. 3,835,176). According to this process, however, α-cyano-benzyl esters are also obtained only in moderate yields.

Furthermore, it is known that, in the reaction of acid-chlorides with substituted benzaldehydes and alkali metal cyanides, the yields of α-cyano-benzyl esters can be improved and the reaction times greatly reduced when the reactions are carried out in multi-phase systems comprising a small amount of water, if appropriate solid alkali metal cyanide and aprotic solvents, if appropriate using phase transfer catalysts (see DE-OS (German Published Specification) No. 2,708,590/U.S. Pat. Nos. 4,110,360, 4,110,363 and 4,123,451).

Furthermore, DE-OS (German Published Specification) No. 2,708,590 discloses that α-phenyl-alkanecarboxylates can be obtained by the reaction of the corresponding acid-chlorides, alkali metal cyanide and benzaldehyde in a two-phase solvent system when special reaction conditions, such as a certain ratio of the amount of water to cyanide, are used. The α-cyano-phenoxybenzyl alkenylcyclopropanecarboxylates which are of particular interest as pesticides can be prepared in high yields in this manner, according to DE-OS (German Published Specification) No. 2,708,590, only when phase transfer catalysts are used for a short reaction time.

Finally, it is known that certain α-cyano-3-phenoxy-benzyl (cyclo)-alkanecarboxylates are also obtained in high yields without using phase transfer catalysts for a short reaction time when aqueous solutions or suspensions of water-soluble cyanides are added to mixtures of the corresponding (cyclo)-alkanecarboxylic acid-chlorides and phenoxybenzaldehydes in hydrocarbons, while stirring vigorously (see DE-OS (German Published Specification) No. 2,933,496).

The present invention now provides a process for the preparation of an α-cyano-3-phenoxy-benzyl 3-alkenyl-2,2-dimethyl-cyclopropanecarboxylate of the general formula

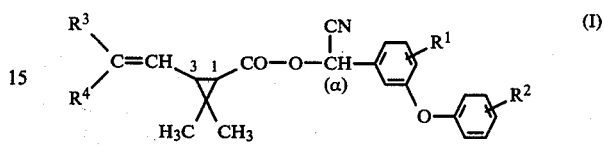

in which

R$^1$ and R$^2$ independently of each other represent a hydrogen or halogen atom, R$^3$ represents a hydrogen or halogen atom or an optionally substituted alkyl group and R$^4$ represents a halogen atom, an optionally substituted alkyl or alkenyl group or an optionally substituted phenyl group or, together with R$^3$, represents an alkanediyl (alkylene) radical, characterized in that a 3-alkenyl-2,2-dimethyl-cyclopropanecarboxylic acid-chloride of the general formula

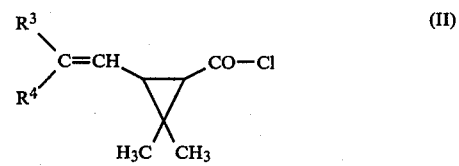

in which

R$^3$ and R$^4$ have the meanings given above, is reacted with a 3-phenoxy-benzaldehyde of the general formula

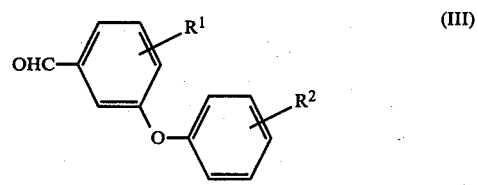

in which

R$^1$ and R$^2$ have the meanings given above, or an adduct thereof with an alkali metal bisulphite (hydrogen sulphite or pyrosulphite), and an alkali metal cyanide, using an alkyl ester of a C$_1$ to C$_6$ carboxylic acid and water as diluents, if appropriate with the addition of an alkali metal bisulphite, at a temperature between −5° and +25° C.

It is to be regarded as surprising that the use of carboxylic acid esters as diluents makes possible the preparation of cyanohydrin esters of the formula (I) in almost quantitative yield and high purity, since it was to be assumed on the basis of the prior art that nonpolar, virtually water-immiscible solvents which are hydrocarbons are the optimum diluents.

In comparison with the use of other solvents, the highest reaction rate is achieved when a carboxylic acid ester is used as a diluent.

A particular advantage of the process according to the invention, however, is that the formation of the various stereoisomers of compounds of the formula (I) can be controlled in such a manner that the proportion of the isomers of relatively high insecticidal action can be substantially increased in comparison with known processes-by the choice of the solvent alone or also by additives such as alkali metal bisulphites.

If, for example, 3-(2,2-dichlorovinyl)-2,2-dimethyl-cyclopropanecarboxylic acid-chloride and 3-phenoxybenzaldehyde in methyl acetate, and an aqueous solution of sodium cyanide, are used as starting materials, the reaction according to the present invention is illustrated by the following equation:

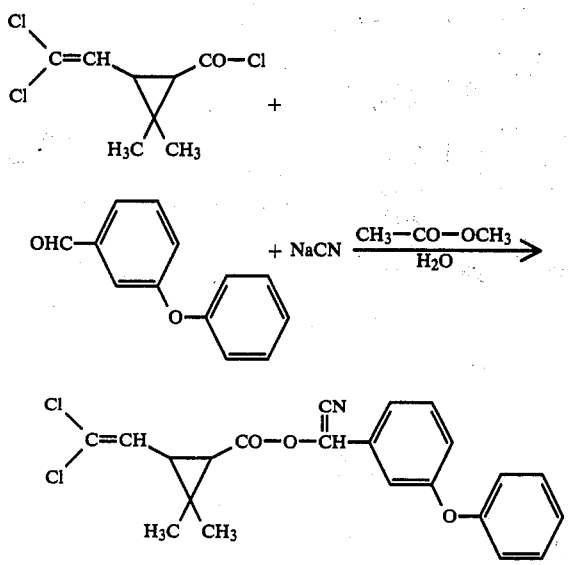

Preferred 3-alkenyl-2,2-dimethyl-cyclopropanecarboxylic acid-chlorides of formula (II) to be used as starting materials are those in which $R^3$ represents a hydrogen, fluorine, chlorine or bromine atom or a methyl or trifluoromethyl group, and $R^4$ represents a fluorine, chlorine or bromine atom, a $C_1$ to $C_5$ alkyl, $C_1$ or $C_2$ fluoroalkyl or $C_1$ or $C_2$ chlorofluoroalkyl group, or a phenyl group which is optionally substituted by fluorine, chlorine or bromine and/or by one or more optionally fluorine-substituted or chlorine-substituted radicals selected from $C_1$ to $C_4$ alkyl, $C_1$ to $C_4$ alkoxy, $C_1$ to $C_4$ alkylthio and $C_1$ or $C_2$ alkylenedioxy, or the two radicals $R^3$ and $R^4$ together represent a $C_2$ to $C_5$ alkanediyl (alkylene) radical.

Preferred 3-phenoxy-benzaldehydes of formula (III) further to be used as starting materials are those in which $R^1$ represents a hydrogen or fluorine atom, and $R^2$ preferably represents a hydrogen, fluorine, chlorine or bromine atom.

Particularly preferred starting compounds of the formula (II) are those in which $R^3$ represents a fluorine, chlorine or bromine atom, and $R^4$ represents a fluorine, chlorine or bromine atom or a $C_1$ or $C_2$ fluoroalkyl, phenyl, 4-fluorophenyl or 4-chlorophenyl group.

A particularly preferred starting compound of the formula (III) is that in which $R^1$ represents 4-fluoro and $R^2$ represents a hydrogen atom (i.e. 4-fluoro-3-phenoxybenzaldehyde).

The following may be mentioned as examples of the starting materials of the formula (II): 3-(2,2-dichlorovinyl)-, 3-(2,2-difluoro-vinyl)-, 3-(2,2-dibromovinyl)-, 3-(2-chloro-3,3,3-trifluoro-1-propenyl)-, 3-(2-chloro-2-phenyl-vinyl)-, 3-(2-chloro-2-(4-fluorophenyl)-vinyl)- and 3-(2-chloro-2-(4-chloro-phenyl)-vinyl-2,2-dimethylcyclopropanecarboxylic acid-chloride.

The starting compounds of the formulae (II) and (III) have already been disclosed (see DE-OS (German Published Specification) No. 2,709,264, and British Patent Specification Nos. 1,413,491 and 2,000,764).

Examples of alkali metal cyanides which can be used in the process according to the invention are sodium cyanide and potassium cyanide. Alkyl esters of lower carboxylic acids which can be used as diluents in the process according to the invention are preferably methyl esters, ethyl esters, n- and isopropyl esters, and n-, iso- and sec-butyl esters of formic acid, acetic acid and propionic acid. The following may be mentioned as examples: formic acid methyl ester (methyl formate), formic acid ethyl ester (ethyl formate), acetic acid methyl ester (methyl acetate), acetic acid ethyl ester (ethyl acetate), propionic acid ethyl ester (ethyl propionate) and acetic acid n-butyl ester (butyl acetate).

Examples of alkali metal bisulphites (hydrogen sulphites or pyrosulphites) which can be employed in the process according to the invention are sodium bisulphite and potassium bisulphite. Sodium bisulphite is preferably employed as an additive. In a preferred process variant, alkali metal bisulphites are employed in catalytic amounts.

In a further preferred variant of the process according to the invention, 1:1 adducts of phenoxybenzaldehydes of the formula (III) and alkali metal bisulphites are employed as starting materials.

In the process according to the invention, the reaction temperature is kept between $-5°$ and $+25°$ C., preferably between 0° and 15° C. In general, the process is carried out under normal pressure.

In general between 0.8 and 1.2 mols, preferably between 0.9 and 1.05 mols of 3-phenoxy-benzaldehyde of the formula (III) and 1 to 2 mols, preferably 1.1 to 1.4 mols of cyanide are employed per mol of 3-alkenyl-2,2-dimethylcyclopropanecarboxylic acid-chloride of the formula (II).

1 to 200 parts by volume, preferably 20 to 120 or 1 to 3 parts by volume, of water are employed per 100 parts by volume of the alkyl ester of a $C_1$ to $C_6$ carboxylic acid.

In a preferred embodiment of the process according to the invention, the starting compounds of the formulae (II) and (III) are dispersed in the carboxylic acid ester used as the diluent, and the aqueous cyanide solution is slowly metered in while stirring vigorously. The reaction mixture is stirred until the end of the reaction and is then diluted, if appropriate, with water and the carboxylic acid ester. The organic phase is separated off, washed with water, dried, and freed from the solvent in vacuo, the product of the formula (I) remaining as an oily residue.

In a further preferred embodiment of the process according to the invention, the starting compounds of the formula (III) and the alkali metal cyanide are dispersed in the carboxylic acid ester used as the diluent, which then preferably contains 1 to 3 parts of water, and the starting compound of the formula (II) is added dropwise. The reaction mixture is stirred until the end of the reaction; the alkali metal chloride formed as the coupling product is separated off by filtration (filtration under suction), and the solvent is distilled off from the filtrate under reduced pressure. The product, of the formula (I), which remains in the residue can be further purified by customary methods.

The products of the formula (I) have 3 asymmetric carbon atoms and accordingly contain 8 optical isomers. An R configuration and an S configuration are possible in each case at the 3 asymmetric carbon atoms—the cyclopropane carbon atoms 1 and 3 and the benzyl carbon atom α. By means of quantitative high-pressure liquid chromatography (HPLC) of the products of the formula (I), 4 diastereomer pairs can be determined, and these are abbreviated as follows, the symbols cis-1 R, cis-1 S, trans-1 R and trans-1 S being used instead of the abbreviations 1 R/3 R, 1 R/3 S, 1 S/3 S and 1 S/3 R for the purpose of increased clarity in establishing the configuration at the cyclopropane skeleton:

I cis-1 R, α R
cis-1 S, α S

II cis-1 R, α S
cis-1 S, α R

III trans-1 R, α R
trans-1 S, α S

IV trans-1 R, α S
trans-1 S, α R

By means of the process according to the present invention, products are obtained in which the proportion of the diastereomer pairs II and IV, which exhibit higher insecticidal activity than the diastereomer pairs I and III, is substantially higher than in the case of the known preparation processes.

The present invention also provides a method of combating pests (especially insects) which comprises applying to the pests, or to a habitat thereof, a compound produced by the process of the present invention alone or in the form of a composition containing as active ingredient a compound of the present invention in admixture with a diluent or carrier.

The present invention also provides a method of freeing or protecting domesticated animals from parasites which comprises applying to said animals a compound produced by the process according to the present invention, in admixture with a diluent or carrier.

The present invention further provides crops protected from damage by pests by being grown in areas in which immediately prior to and/or during the time of the growing a compound produced by the process of the present invention was applied alone or in admixture with a diluent or carrier.

It will be seen that the usual methods of providing a harvested crop may be improved by the present invention.

The present invention further provides domesticated animals whenever freed or protected from parasites by the application to said animals of a compound produced by the process according to the present invention, in admixture with a diluent or carrier.

The examples which follow illustrate the process according to the present invention:

EXAMPLE 1

Preparation of 4-fluoro-3-phenoxy-benzyl 3-(2,2-dichlorovinyl)-2,2-dimethyl-cyclopropanecarboxylate (1) in ethyl acetate/water (two-phase medium)

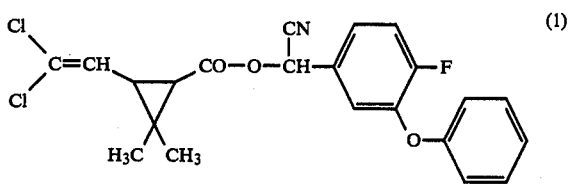

239.5 g (1 mol) of 3-(2,2-dichloro-vinyl)-2,2-dimethyl-cyclopropanecarboxylic acid-chloride and 218.2 g of 4-fluoro-3-phenoxy-benzaldehyde (1 mol) were initially introduced into 1 liter of ethyl acetate, under an argon atmosphere. A solution of 58.8 g (1.2 mols) of sodium cyanide in 200 ml of water was added dropwise in the course of 30 minutes, while stirring very vigorously (approximately 1,500 revolutions per minute) and while cooling externally with ice water (internal temperature 0° to 10° C.), and the reaction mixture was stirred for a further 3 hours at 5° to 10° C. The mixture was then diluted with 100 ml of water, and the organic phase was separated off, washed twice with 300 ml of water, dried with 40 g of sodium sulphate, and freed from the solvent by vacuum distillation. 430.2 g of (1) were obtained as a brownish viscous oil. The yield was 91.5% of theory (100% pure) according to HPLC analysis.

Isomer ratio (I+III):(II+IV)=56:44.

In an analogous experiment using toluene as the diluent, the following isomer ratio resulted: (I+III):(II+IV)=65.5:34.5.

EXAMPLE 2

Effect of the solvent on the reaction rate in the preparation of (1)

A number of experiments were carried out analogously to Example 1, and only the solvent was varied. The time which elapsed until the starting materials of the formulae (II) and (III) were no longer detectable by thin layer chromatography is given in the following Table as the "Reaction time".

| Solvent (1/1 mol) | Reaction time (hours) |
|---|---|
| Toluene | 16 |
| Xylene | 12 |
| Cyclohexane | 9 |
| Butyl acetate | 4 |
| Ethyl acetate | 2–3 |
| Methyl acetate | 2–3 |
| Ethyl formate | 2–3 |

Reaction temperature: 0° to 5° C. (prior art 20° to 25° C.).

EXAMPLE 3

Effect of sodium bisulphite on the distribution of isomers in the preparation of (1)

A series of experiments with various added amounts of bisulphite solution were carried out. 21.6 g of 3-phenoxy-4-fluoro-benzaldehyde (0.1 mol) and 20 ml of ethyl acetate, and a varied amount of 40% strength sodium bisulphite solution:

Experiment 1: 26.0 g (0.1 mol) of NaHSO$_3$
Experiment 2: 13.0 g (0.05 mol) of NaHSO$_3$
Experiment 3: 6.5 g (0.025 mol) of NaHSO$_3$
Experiment 4: 0 were initially introduced into 500 ml stirred flasks in each case.

(1) 24.2 g (0.1 mol) of 3-(2,2-dichloro-vinyl)-2,2-dimethyl-cyclopropanecarboxylic acid-chloride and
(2) aqueous sodium cyanide solution, in particular in Experiment 1: 11.0 g of NaCN+22 g of H$_2$O (0.22 mol of NaCN)
Experiment 2: 8.8 g of NaCN+17.6 g of H$_2$O (0.18 mol of NaCN)
Experiment 3: 7.6 g of NaCN+15.2 g of H$_2$O (0.155 mol of NaCN)
Experiment 4: 5.9 g of NaCN+13 g of H$_2$O (0.12 mol of NaCN)

were simultaneously added dropwise to the mixture, while stirring at an internal temperature of 20° C.

The duration of dropwise addition was approximately 30 minutes. The mixture was then stirred vigorously for a further period until the aldehyde spot in the thin layer chromatogram (silica gel/toluene) had vanished. This period lasted:

approximately 30 minutes in Experiment 1
approximately 30 minutes in Experiment 2
approximately 1 hour in Experiment 3
approximately 2 hours in Experiment 4.

The effective stirring time was approximately 1 hour longer in each case (time for preparing and evaluating the chromatogram).

To work up the mixture, 80 ml of ethyl acetate and 50 ml of water were added in each case, the phases were separated, the organic phase was rinsed with twice 40 ml of water and dried with a little sodium sulphate, and the solvent was removed in vacuo. The following values of the isomer ratio (I+III):(II+IV) were obtained by HPLC analysis:

Experiment 1: 52.3:47.7
Experiment 2: 55.1:44.9
Experiment 3: 57.6:42.4
Experiment 4: 59.9:40.1

EXAMPLE 4

Preparation of (1) in a single-phase medium

Use of ethyl acetate with a 2% water content 125 g (0.525 mol) of 3-(2,2-dichloro-vinyl)-2,2-dimethyl-cyclopropanecarboxylic acid-chloride (95.7% strength) were added dropwise, while stirring, to a mixture, cooled to 0° to 5° C., of 109 g (0.5 mol) of 4-fluoro-3-phenoxy-benzaldehyde, 44.2 g (0.625 mol) of potassium cyanide (92.1% strength) and 300 g of ethyl acetate (water content 2%). The reaction mixture was stirred at 0° to 5° C. (approximately 150 minutes) until aldehyde could no longer be detected by thin layer chromatography (silica gel/toluene). To work up the mixture, it was filtered off under suction and rinsed with 80 g of ethyl acetate, and the solvent was distilled off from the filtrate under reduced pressure. For the purification, the product remaining in the residue was taken up in 400 ml of toluene, the solution was washed with 100 ml of water, and the product was freed from the solvent again by distillation under reduced pressure (kept for a further hour at 80° C./2 mbar when dry). 217 g (93% of theory) of (1) were obtained as a brownish yellow, clear and viscous oil with a purity of 93.2%.

Proportions of the diastereomer pairs I to IV:
I: 25.5%
II: 17.9%
III: 29.8%
IV: 20.0%

(The % data relate to percentages by weight, unless indicated otherwise).

It is understood that the specification and examples are illustrative but not limitative of the present invention and that other embodiments within the spirit and scope of the invention will suggest themselves to those skilled in the art.

We claim:

1. A process for the preparation of α-cyano-3-phenoxybenzyl 3-alkenyl-2,2-dimethyl-cyclopropanecarboxylate of the formula

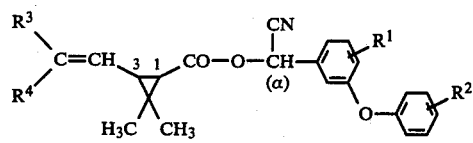

in which
 $R^1$ and $R^2$ each independently is a hydrogen or halogen atoms,
 $R^3$ is a hydrogen or halogen atom or an optionally substituted alkyl group, and
 $R^4$ is a halogen atom, an optionally substituted alkyl or alkenyl group or an optionally substituted phenyl group, or, together with $R^3$, is an alkanediyl radical, comprising reacting a 3-alkenyl-2,2-dimethyl-cyclopropanecarboxylic acid-chloride of the formula

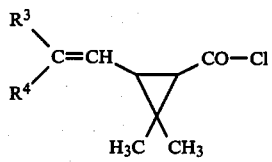

with a 3-phenoxy-benzaldehyde of the formula

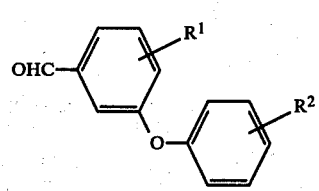

or an adduct thereof with an alkali metal bisulphite (hydrogen sulphite or pyrosulphite), and an alkali metal cyanide, in the presence of an alkyl ester of a C$_1$ to C$_6$ carboxylic acids and water as diluents at a temperature between about −5° and +25° C.

2. A process according to claim 1, wherein the reaction is carried out with the addition of an alkali metal bisulphite.

3. A process according to claim 1, in which
$R^1$ is a hydrogen or fluorine atom,
$R^2$ is a hydrogen, fluorine, chlorine or bromine atom,
$R^3$ is a hydrogen, fluorine, chlorine or bromine atom or a methyl or trifluoromethyl group, and
$R^4$ is a fluorine, chlorine or bromine atom, a $C_1$ to $C_5$ alkyl, $C_1$ to $C_2$ fluoroalkyl or $C_1$ or $C_2$ chlorofluoroalkyl group, or a phenyl group which is optionally substituted by fluorine, chlorine or bromine and/or by at least one optionally fluorine-substituted or chlorine-substituted radicals selected from $C_1$ to $C_4$ alkyl, $C_1$ to $C_4$ alkoxy, $C_1$ to $C_4$ alkylthio and $C_1$ or $C_2$ alkylenedioxy, or the two radicals $R^3$ and $R^4$ together are a $C_2$ to $C_5$ alkanediyl radical.

4. A process according to claim 1, in which
$R^1$ is 4-fluoro,
$R^2$ is a hydrogen atom,
$R^3$ is a fluorine, chlorine or bromine atom, and
$R^4$ is a fluorine, chlorine or bromine atom or a $C_1$ or $C_2$ fluoroalkyl, phenyl, 4-fluorophenyl or 4-chlorophenyl group.

5. A process according to claim 1, wherein the reaction is carried out at a temperature between about 0° and 15° C.

6. A process according to claim 1, wherein between about 0.8 and 1.2 mols of the 3-phenoxy-benzaldehyde and about 1.1 to 1.4 mols of alkali metal cyanide are employed per mol of 3-alkenyl-2,2-dimethylcyclopropanecarboxylic acid-chloride.

7. A process according to claim 1, wherein about 1 to 200 parts by volume of water are employed per 100 parts by volume of the alkyl ester of a $C_1$ to $C_6$ carboxylic acid.

8. A process according to claim 1, wherein about 1 to 3 parts by volume of water are employed per 100 parts by volume of the alkyl ester of a $C_1$ to $C_6$ carboxylic acid.

9. A process according to claim 1, wherein the 3-phenoxy-benzaldehyde is employed as the adduct with an alkali metal bisulphite (hydrogen sulphite or pyrosulphite).

10. A process according to claim 1, wherein the alkali metal bisulphite (hydrogen sulphite or pyrosulphite) or adduct with the 3-phenoxy-benzaldehyde is employed in a catalytic amount.

11. A process according to claim 1, wherein the alkali metal cyanide is sodium cyanide or potassium cyanide.

12. A process according to claim 4, wherein the reaction is carried out at a temperature between 0° and 15° C. and about 0.8 and 1.2 mols of the 3-phenoxybenzaldehyde and about 1.1 to 1.4 mols of alkali metal cyanide are employed per mol of 3-alkenyl-2,2-dimethylcyclopropanecarboxylic acid chloride, about 1 to 3 parts by volume of water are employed per 100 parts by volume of the alkyl ester of a $C_1$ to $C_6$ carboxylic acid, and the alkali metal cyanide is sodium cyanide or potassium cyanide.

* * * * *